United States Patent [19]
Gudin et al.

[11] Patent Number: 5,536,654
[45] Date of Patent: Jul. 16, 1996

[54] PROCESS FOR THE PRODUCTION AND EXTRACTION OF THERMOSTABLE SUPEROXIDE-DISMUTASES FROM A PHOTOSYNTHETIC MICROORGANISM CULTURE

[75] Inventors: Claude Gudin, Aix En Provence; Claudine Trezzy, Le Rove, both of France

[73] Assignee: Heliosynthese S.A. Centre d'Affaires Actimark Bureau, Aix En Provence Cedex, France

[21] Appl. No.: 257,657

[22] Filed: Jun. 9, 1994

[30]  Foreign Application Priority Data

Jun. 11, 1993 [FR] France .................................. 93 07057

[51] Int. Cl.⁶ ..................................................... C12N 9/02
[52] U.S. Cl. ........................ 435/189; 435/257.1; 435/814
[58] Field of Search ................................. 435/189, 257.1, 435/814

[56]  References Cited

U.S. PATENT DOCUMENTS

| | | | |
|---|---|---|---|
| 4,868,123 | 9/1989 | Berson et al. | 435/290 |
| 5,179,012 | 1/1993 | Gudin et al. | 435/125 |

FOREIGN PATENT DOCUMENTS

| | | |
|---|---|---|
| 0218480 | 4/1987 | European Pat. Off. . |
| 0437393 | 7/1991 | European Pat. Off. . |
| 0533942 | 3/1993 | European Pat. Off. . |
| 2635531 | 2/1990 | France . |
| 2656874 | 7/1991 | France . |
| 2674458 | 10/1992 | France . |
| 2685346 | 6/1993 | France . |

OTHER PUBLICATIONS

Derwent Abs. J06069181 (Mar. 1990) Idemitsu Petrochem KK.

Patent Abstracts of Japan, vol. 014, No. 250 (C–0723) 29 May 1990 & JP–A–02 069 181 (Tadashi Matsunaga) 8 Mar. 1990.

Health Physics, vol. 53, No. 3, Sep. 1987, New York, pp. 281–286, Conter A. et al., "Radiation Stimulation During the Early Stationary Growth Phase in Synechococcus Lividus and its Correlation with Photooxidative Stress Occurring before the Stationary Phase".

Biochim. Biophys. Acta, vol. 438, No. 2, 8 Jul. 1976, pp. 380–392, Lumsden et al., "Purification and Physicochemical Properties of Superoxide Dismutase from Two Photosynthetic Microorganisms".

Primary Examiner—Herbert J. Lilling
Attorney, Agent, or Firm—Pearne, Gordon, McCoy & Granger

[57]  ABSTRACT

Process for the production and extraction of thermostable super-oxide-dismutases from a photosynthetic microorganism cell. The thermostable superoxide-dismutase production and extraction process consists a) of culturing in the temperature range 40° to 80° C., in a closed photoreactor made from a light-transparent material and which is thermally resistant within said range, aerobic, photosynthetic, thermophilic microorganisms, which produce oxygen and grow exponentially in said range, said microorganisms being suspended in a culture medium and chosen from among microalgae and cyanobacteria and b) extracting from the culture medium the freshly produced, thermostable superoxide-dismutases, by cellular crushing, ultrafiltration and selective precipitation.

10 Claims, 1 Drawing Sheet

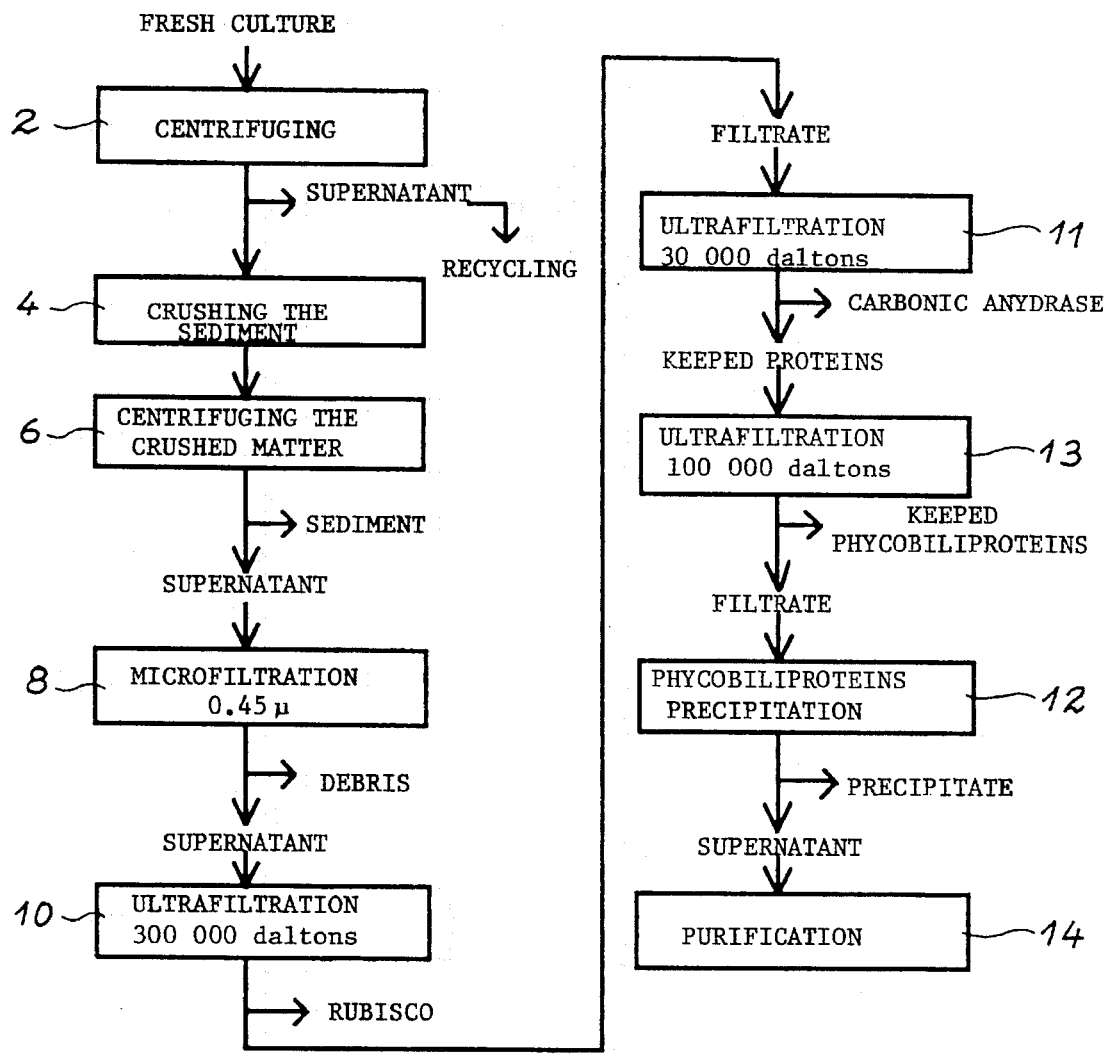

PROCESS FOR THE PRODUCTION AND EXTRACTION OF THERMOSTABLE SUPEROXIDE-DISMUTASES FROM A PHOTOSYNTHETIC MICROORGANISM CULTURE

DESCRIPTION

The present invention relates to a process for the production and extraction of thermally stable superoxide-dismutases from a photosynthetic microorganism culture suspended in a liquid medium. The process permits an intense, controlled production of thermostable superoxide-dismutases (SOD) on an industrial scale. In particular, these SOD's are thermostable up to 80° C.

SOD's are catalysts of the dismutation of superoxide ions. They are also used in acute phenomena for the release of superoxide radicals or in aging phenomena.

Thus, the SOD's according to the invention are intended for use in the pharmaceutical field, as anti-inflammatories (rheumatism, arthritis), cosmetological field as anti-aging products and for protecting the skin and hair in particular against ultraviolet rays, agroalimentary field for protecting oils and fatty substances, as colouring regulating agents, in the agricultural field as fertilizers, as well as in the biomedical field.

SOD's are formed by two interlinked peptide subunits. They are placed in three categories as a function of the type of metal used in their formation, Cu/Zn SOD's having a human or animal origin, Fe SOD's frequently encountered in aerobic bacteria and Mn SOD's. The SOD's according to the invention form part of the third category, the Fe or Cu/Zn SOD's occurring in an accessory manner.

Most of the presently produced and used SOD's are destroyed when subject to a heat treatment at above 40° C. such as e.g. pasteurization or sterilization requiring temperatures of approximately 70° C. Thus, the SOD having an animal origin is destroyed as from 37° C. However, it is desirable to use sterilized products in cosmetology, as well as in the pharmaceutical and biomedical fields.

In addition, a resistance at 50° C. of SOD's or SOD-rich extracts would make it possible to speed up the study of the aging of cosmetological products under economic conditions. Recent research has been carried out in different laboratories for the production of thermostable SOD's.

Thus, document (1) by A. Hosono et al ("Superoxide-dismutase activity in the crude cell extract from *Streptococcus salivarius* subspecies *thermophilus* 3535" Anim Sci. Technol. Jpn., 62, 1991, pp. 39–44) compares the production of SOD by seven anaerobic lactic bacterial strains and studies the stability of these enzymatic activities as a function of the pH and temperature. The thermal stability is obtained for the SOD produced by *Streptococcus salivarius, thermophilus,* subspecies, which remain stable when subject to a heat treatment at 60° C. for 30 minutes, but then starts to decompose for a heat treatment at 70° C.

Document (2) by R. A. Hallewel et al ("Thermostabilization of recombinant human and bovine Cu/Zn superoxide-dismutases by replacement of free cysteines", Biochem. and Biophys. Research Communications, vol. 181, No. 1, 1981, pp. 474–480) describes the increase in the thermostability of human or bovine SOD obtained by mutation on yeasts containing the gene coding for SOD, on removing a free cysteine residue entering in the amino acid composition of the enzymatic protein.

In document (3) by K. B. Searcy and D. G. Searcy ("Superoxide-dismutase from the archaebacterium *Thermoplasma acidophilum*" Biochimica et Biophysica Acta, 670, 1991, pp. 39–46), a description is given of the culture of an aerobic bacterium at 59° C. and a pH of 1 to 2 producing a SOD containing iron and zinc having, after a heat treatment at 100° C., an enzymatic activity equal to 71% of that obtained after a treatment at 30° C., the latter also being equal to that measured before any treatment.

The different thermostable SOD's described in these documents are oxygen-consuming heterotrophic species, which leads to a biosynthesis of SOD regulated by the oxygen concentration dissolved in the culture medium. However, these oxygen-consuming species constantly lower the level of the oxygen, which then becomes a factor limiting the growth of said species and therefore the production of SOD's.

Thus, the known thermostable SOD production processes do not permit an intense, industrial production of thermostable SOD's able to resist hot sterilization stages.

The invention specifically relates to a novel process for the production and extraction of thermostable superoxide-dismutases using photosynthetic microorganisms, i.e. able to transform by means of solar energy carbon dioxide into biomass with the main byproduct of said biochemical transformation the production of oxygen.

Thus, these photosynthetic species constantly raise the oxygen level in the culture medium thus increasing SOD production by the reacting microorganisms with respect to this highly oxidizing medium.

Thus, the invention relates to a process for the production and extraction of thermostable superoxide-dismutases consisting a) of culturing in the temperature range 40° to 80° C., in a closed photoreactor made from a light transparent material thermally resistant within said range, aerobic, photosynthetic, thermophilic microorganisms, which produce oxygen and grow exponentially in said temperature range, said microorganisms being suspended in a culture medium and chosen from among microalgae and cyanobacteria and b) extracting from the culture medium the freshly produced, thermostable superoxide-dismutases. The microalgae to which the present invention applies fall in the class of Chlorophyceae or Rhodophyceae. As examples of microalgae usable in the invention, reference can be made to Chlorella such as *Chlorella vulgaris* and *Chlorella saccharophila*, Dunaliella such as *Dunaliella salina*, Cyanidium such as *Cyanidium caldarium*.

Cyanobacteria, also known under the name blue algae, produce as microalgae and unlike other bacteria, oxygen by photosynthesis and Mn SOD's and their behaviour in the oxidizing medium, as well as their culture are highly comparable with those of microalgae.

As cyanobacteria to which the present invention applies, reference can be made to the following: Chroococcacae, Stigonemataceae, Mastigocladacae, Oscillatroriacae. As examples, reference can be made to Synechococcus such as *Synechococcus lividus* and *Synechococcus elongatus*; Synechocystis such as *Synechocystis minervae*; Mastigocladus such as *Mastigocladus laminosus*; Phormidium such as *Phormidium laminosus*; Symploca such as *Symploca thermalis*; Aphanocapsa such as *Aphanocapsa thermalis;* or *Fisherella*.

The culture of photosynthetic microorganisms takes place in natural sunlight. Moreover, with a view to increasing SOD production by increasing the photosynthesis period and therefore the production of oxygen, it is preferable to culture the microorganisms by superimposing on the natural sunlight artificial lighting which can be maintained over night. Moreover, with a view to increasing SOD production, it is advantageous to enrich the culture medium with oxygen and/or carbon dioxide gas.

The $O_2$ and/or $CO_2$ can be supplied by injecting said gases in molecular form or as air into the photoreactor. It is also possible to increase the $O_2$ quantity in the photoreactor by limiting its evacuation from the photoreactor and/or by reinjecting it into the photoreactor.

In order to improve the thermal stability of the SOD's produced, said SOD's are extracted in the temperature range 40° to 80° C. In particular, extraction takes place at the same temperature as that used for culturing the microorganisms.

According to the invention, production and extraction of the thermostable SOD's take place in linear, continuous form.

Advantageously, the superoxide-dismutase extraction stage consists of:

i) separating the microorganisms from the culture medium, ii) crushing the microorganisms obtained in i) in order to extract therefrom a liquid containing superoxide-dismutases and other proteins, iii) concentrating said liquid, iv) separating said other proteins selectively with respect to the superoxide-dismutases.

Advantageously, the concentration of the liquid produced by the crushed microorganisms is carried out by microfiltration and the SOD's are separated from the other proteins by selective ultrafiltration. A range of diaphragms or membranes (300,000, 100,000 and 30,000 daltons) makes it possible to separate the large proteins (such as Rubisco) from the phycobiliproteins (100,000 to 200,000 daltons) and the small proteins such as carbonic anhydrase. The SOD's appear in the fraction of the phycobiliproteins, which are then precipitated by ammonium sulphate, the SOD remaining in the supernatant product.

The thermostable properties of the SOD's produced by the process according to the invention are not solely due to the heating of the culture medium between 40° and 80° C., but also to the fact that said SOD's are produced by thermophilic microorganisms, which have their growth optimum in the thermophilic zone of 40° to 80° C. Thus, a strain of microorganism developing below said optimum growth conditions will produce a generally non-thermostable SOD.

The culture medium can be heated by using hot water from the thermal system and/or using closed photoreactors having a favourable surface/volume ratio, i.e exceeding 10, in very sunny regions.

The term transparent material thermally resistant at between 40° and 80° C. means a material remaining light transparent without opacifying or embrittling when used in this temperature range. Preferably, the photoreactor is made from a material able to withstand a temperature above 120° C. Examples of such material are glass or polymethyl methacrylate (Plexiglass®).

Other features and advantages of the invention can be gathered from the following illustrative, non-limitative description with reference to the single drawing illustrating the different stages of the process according to the invention.

The process for the production of thermostable SOD's at between 40° and 80° C. firstly consists of culturing in a closed photobioreactor and thus under aerobic conditions, thermophilic, photosynthetic, oxygen-producing microalgae or cyanobacteria. The photoreactor is in particular that described in document (4), i.e. FR-A-2,656,874, which has transparent tubes in which circulates the culture medium containing the microorganisms and made, according to the invention, from glass. This photoreactor can also be equipped with the automatic tube cleaning device as described in document (5), i.e. FR-A-2,674,458, as well as with the air lift system described in document (6), i.e. FR-A-2,685,344.

The culture medium in which are suspended the microorganisms is a function of the latter. Thus, culturing can take place with soft or sea water with a pH between 1 and 8. The culture medium is also heated to a temperature chosen between 40° and 80° C., which is a function of the cultured, photosynthetic microorganisms. This temperature is chosen so as to correspond to the optimum growth temperature of the thermophilic microorganism used.

The following table I gives different examples of microorganisms usable in the invention, as well as their optimum growth temperature, the nature of the water used for culturing and the pH of the culture medium.

For cyanobacteria, the nutrient substrate used is medium BG11, whose composition is in particular given in document (7) ("Generic assignments, strain histories and properties of pure cultures of Cyanobacteria", by R. Rippka et al., Journal of General Microbiology, vol. 111, 1979, p.4).

For *Dunaliella salina*, use is made of the nutrient medium described in document (8) by Pick et al, ("Plant physiol."81, 1986, pp. 92–96).

For *Cyanidium caldarium* use is made of the Allen medium described in reference (9), (Allen, NB-1959, Arch. Mikrobiol. 32, pp. 270–277).

For Chlorella, use is made of the BB medium described in document (10) by H. W. Nichols and H. C. Bold (J. Phycol. 1, 1965, pp. 34–38).

The production of microalgae and cyanobacteria takes place under natural lighting conditions and in particular in very sunny regions. Advantageously, said lighting is supplemented by artificial lighting of the daylight type, such as in a greenhouse in order to extend the natural photoperiod and the photosynthetic oxygen production, particularly when the sun has disappeared, in order to increase SOD production.

In addition, the culture medium is enriched with oxygen and/or carbon dioxide, as described in document (4), with the aid of a carbonator and a system for the recovery and reinjection of oxygen supplied by the microorganisms during the photosynthesis into the culture medium.

The residence time of the microorganisms in the culture medium is a function of their constitution and varies between 12 hours and 15 days.

The linear extraction of thermostable SOD's takes place in the exponential microorganism growth stage, i.e. on a fresh culture.

As shown in the drawing, thermostable SOD extraction firstly consists of centrifuging, as indicated in (2), the culture at between 10,000 and 30,000 g for 30 min. The thus produced supernatant product can be recycled into the photobioreactor with a view to a continuous culture.

According to the invention, the centrifuging 2 is preferably performed whilst maintaining the culture medium at the temperature which it had in the photoreactor.

The sediment from the centrifuging process 2 is then crushed, as indicated at 4, with the aid of an industrial press in order to undergo a pressure/vacuum cycle in a homogenizer operating at a pressure of $2.10^7$ Pa. Crushing in particular takes place hot at between 40° and 80° C.

As shown at 6, this is followed by a further centrifuging of the cellular crushed matter obtained in a continuous centrifuge rotating at between 10,000 and 45,000 g for 1 h. The sediment from said centrifuging 6 essentially contains cellular residues. It can be utilized for the fatty acids contained therein.

The supernatant product of the centrifuging process 6 contains thermostable SOD, as well as phycobiliproteins. The proteins have a molecular weight between 120,000 and 240,000 daltons and an isoelectric point from 4.5 to 5.11. Centrifuging 6 is performed at the temperature used for the growth of the microalgae or cyanobacteria.

The supernatant product then undergoes a microfiltration 8 at 0.45μ and then a first ultrafiltration 10 using a filter membrane with a cutoff threshold of 300,000 daltons in order to separate the large proteins, such as Rubisco, from average proteins such as phycobiliproteins (100,000 to 200,000 daltons) and small proteins such as carbonic anhydrase.

This is followed by a further ultrafiltration 11 with a 30,000 dalton membrane in order to separate the small proteins from the average proteins and then a third ultrafiltration 13 with a 100,000 dalton membrane to separate most of the phycobiliproteins from the SOD.

These microfiltrations and said ultrafiltration are advantageously carried out at the microorganism culturing temperature.

The concentrate or filtrate is collected and to it is added ammonium sulphate. The sulphate quantity used represents 10 times the weight of the collected concentrate. This ammonium sulphate permits the precipitation 12 of the residual phycobili-proteins.

According to the invention, the precipitation 12 is carried out at the microorganism culturing temperature.

The supernatant product containing the concentrated thermostable SOD's is then purified as indicated at 14 by gas or liquid chromatography. These SOD's are Mn 30,000 to 80,000 dalton macromolecules with an isoelectric point of approximately 4.2. These SOD's can then be sterilized or pasteurized with a view to their use in cosmetics and medicaments.

Thermostable SOD production examples are given hereinafter.

EXAMPLES 1 TO 4

Under the conditions described hereinbefore, culturing takes place of the three following thermophilic species: *Synechococcus lividus; Mastigocladus laminosus* and *Cyanidium caldarium*. The culture conditions and SOD quantities produced expressed by mg of dry matter are given in the following table II.

Counter-Examples 1 and 2

In parallel, culturing took place of mesophilic species such as *Porphyridium cruentum* and *Skeletonema costatum*, in a reactor identical to that used for the above thermophilic species and the SOD quantity produced by these mesophilic species was measured. The results are given in table II.

The SOD quantity is determined according to the Nitroblue Tetrazolium, NBT, method or the Xanthine Oxydase, XO, method. These measuring methods are in particular described in document (11) by A. N. Michelson et al ("Superoxides and superoxide-dismutases" Academic Press, 1977, p.11).

In table II, the SOD quantity indicated corresponds to that obtained before it underwent a heat treatment.

The species of examples 1 to 4 and counter-examples $C_1$, $C_2$ underwent cellular crushing, as described in stage 4 and then underwent a heat treatment.

It can be seen that the thermophilic species ($EX_1$ to $EX_4$) cultured under the conditions described hereinbefore, after 2 hours heating at 50° C., had a SOD quantity representing 100% of that measured prior to the heat treatment. Moreover, after 30 minutes heating at 80° C., 100% of the SOD quantity measured before the heat treatment was obtained.

However, after 30 minutes heating at 60° C., the cellular extracts of the mesophilic species of counter-examples $C_1$ and $C_2$ only had 50% of the SOD quantity measured before the heat treatment.

In examples 1 to 4, the thermophilic species were cultured without oxygen and carbon dioxide enrichment, i.e. with the minimum 0.03% carbon dioxide supply necessary for photosynthesis.

The increase of said $CO_2$ supply leads to a increase in the concentration of photosynthetic cells and therefore the oxygen concentration. Thus, a fixed $CO_2$ molecule leads to the production of an oxygen molecule and therefore an antiradical activity. Thus, by doubling the $CO_2$ supply, it is possible to double the quantity of thermostable SOD's produced.

TABLE I

| Species | Water | Temperature °C. | pH |
| --- | --- | --- | --- |
| Cyanidium caldarium | Soft | 40 to 50 | 1 to 5 |
| * Chlorella vulgaris | Soft | 40 to 50 | neutral |
| * Chlorella saccharophila | Soft | 40 to 60 | neutral |
| * Dunaliella salina | Sea | 40 to 50 | neutral |
| Synechococcus lividus | Soft | 50 to 80 | neutral |
| * Synechococcus elongatus | Soft | 50 to 70 | neutral |
| Synechocystis minervae | Soft | 40 to 60 | neutral |
| Mastigocladus laminosus | Soft | 40 to 60 | neutral |
| Fisherella sp | Soft | 40 to 60 | neutral |
| * Phormidium laminosus | Soft | 40 to 60 | neutral |
| * Symploca thermalis | Soft | 40 to 60 | neutral |
| * Aphanocapsa thermalis | Soft | 40 to 60 | neutral |

* Russian origin.

TABLE II

| Ex/Counter | Culture | | | SOD activity/mg dry matter | |
| --- | --- | --- | --- | --- | --- |
| Ex. | Species | Age (d) | T °C. | XO in unit | NBT in unit |
| Ex. 1 | Synechoccocus lividus | 3.5 | 40 | 6 | — |
| Ex. 2 | Synechoccocus lividus | 3.5 | 50 | 3 | — |
| Ex. 3 | Mastigocladus laminosus | 3.5 | 45 | — | 4 |
| Ex. 4 | Cyanidium | 15 | 40 | 3 | — |

TABLE II-continued

| Ex/Counter Ex. | Culture | | | SOD activity/mg dry matter | |
|---|---|---|---|---|---|
| | Species | Age (d) | T °C. | XO in unit | NBT in unit |
| C₁ | caldarium Porphyridium cruentum | 3 | 15 to 30 | 4.3 | 10 |
| C₂ | Skeletonema costatum | 12 | 15 to 30 | 10 | 5.9 |

We claim:

1. Process for the production and extraction of thermostable superoxide-dismutases, comprising the steps of: a) culturing in the temperature range of 40° to 80° C., in a closed photoreactor made from a light transparent material of a thermally resistant nature within said range, aerobic, photosynthetic, thermophilic, oxygen-producing microorganisms and having exponential growth within said range, said microorganisms being suspended in a culture medium and selected from the group consisting of microalgae and cyanobacteria and b) extracting from the culture medium the freshly produced, thermostable superoxide-dismutases, said extraction being performed at a temperature in the range between 40° and 80° C.

2. Process according to claim 1, characterized in that the culture medium is enriched by oxygen and/or carbon dioxide gas during stage a).

3. Process according to claim 2, wherein the microalgae are selected from the group consisting of Cyanidium, Chlorella and Dunalliella.

4. Process according to claim 3, wherein the cyanobacteria are selected from the group consisting of Synechococcus, Synechocystis, Mastigocladus, Phormidium, Symploca, Aphanocapsa and Fisherella.

5. Process according to claim 4, wherein step a) is carried out in artificial light and/or sunlight.

6. Process according to claim 6, wherein step b) consists of:
   i) separating the microorganisms from the culture medium,
   ii) crushing the microorganisms obtained in i) in order to extract therefrom a liquid containing the superoxide-dismutases and other proteins,
   iii) concentrating the said liquid,
   iv) separating said other proteins in selective manner with respect to the superoxide-dismutases.

7. Process according to claim 6, wherein step iv) comprises several selective ultrafiltration stages and a precipitation stage with ammonium sulphate.

8. Process according to claims 6 or 7, wherein step i) is performed by centrifuging.

9. Process according to any one of the claims 1 to 8, wherein the photoreactor is made from glass.

10. Process according to claim 1, wherein the extraction takes place at the same temperature as used for culturing the microorganisms.

* * * * *